US00PP17225P3

(12) United States Plant Patent
Jensen

(10) Patent No.: US PP17,225 P3
(45) Date of Patent: Nov. 21, 2006

(54) *CAMPANULA* PLANT NAMED 'PKMI0L'

(50) Latin Name: *Campanula lasiocarpa*
Varietal Denomination: PKML01

(75) Inventor: Gert Kim Jensen, Odense N (DK)

(73) Assignee: Gartneriet PKM ApS, Odense N (DK)

( * ) Notice: Subject to any disclaimer, the term of this patent is extended or adjusted under 35 U.S.C. 154(b) by 0 days.

(21) Appl. No.: 11/059,412

(22) Filed: Feb. 17, 2005

(65) Prior Publication Data

US 2006/0185047 P1 Aug. 17, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Union Community Plant Variety Office (CPVO) 2004/2055 filed Nov. 3, 2004—documents include Feb. 28, 2006 print–out from CPVO website verifying application information (1 pg) and Proposal for Variety Denomination (1 pg), Application Papers (7 pgs) and Technical Questionnaire (5 pgs).

Canadian Plant Breeder's Rights 04/4487 filed Nov. 24, 2004—documents include Feb. 28, 2006 print–out from Canadian Food Inspection Agency—Plant Breeders' Rights Office List of Varieties verifying application information (1 pg) and Filing Receipt dated Nov. 26, 2004 (1 pg).

Japanese Plant Variety Rights 17736 filed Dec. 9, 2004—documents include Filing Receipt (w/English Translation) verifying application information (2 pgs) and Plant Variety Rights Application Papers (10 pgs).

*Primary Examiner*—Anne Marie Grunberg
*Assistant Examiner*—Georgia Helmer
(74) *Attorney, Agent, or Firm*—Foley & Lardner LLP

(57) ABSTRACT

A new and distinct cultivar of *Campanula* plant named 'PKML01', characterized by having compact, upright plant habit; dense and bushy plant form; vigorous growth habit and large upright violet-blue flowers.

2 Drawing Sheets

Botanical Designation: *Campanula lasiocarpa.*
Variety Denomination: 'PKML01'.

BACKGROUND OF THE INVENTION

The present invention relates to a new and distinct cultivar of *Campanula* plant, botanically known as *Campanula lasiocarpa* Cham., commonly known as Bellflower, and hereinafter referred to by the name 'PKML01'.

The new *Campanula*, 'PKML01', is a product of a planned mutant selection and monitoring program conducted by the inventor, Gert K. Jensen, in Søhus, Denmark. The objective of the breeding program is to develop a new *Campanula* variety with small violet-blue flowers.

The new *Campanula* cultivar, 'PKML01', was isolated by the inventor in 2002 in Søhus, Denmark, by seedling selection following self-pollination of the maternal *Campanula lasiocarpa* Cham. plant designated '2229' (unpatented). The inventor selected the new *Campanula* cultivar on the basis of its violet-blue flowers and sturdy, compact and freely flowering habit. Plants of the new *Campanula* cultivar are more upright and compact and more freely flowering than plants of the maternal parent.

Asexual reproduction of the new *Campanula* cultivar by terminal cuttings taken and propagated since January of 2002 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKML01'. These characteristics in combination distinguish 'PKML01' as a new and distinct cultivar:

1. Increased quantity of smaller, darker violet-blue flowers per plant;
2. Dense and bushy plant form, mainly due to central ascending, stiff stems; and
3. Upright, globular plant habit.

Plants of the new cultivar, 'PKML01' can be compared to *Campanula lasiocarpa* wild type seedlings. In side-by-side comparisons conducted Søhus, Denmark, plants of 'PKML01' differed from plants of the wild type seedlings in the following characteristics:

1. Plants of 'PKML01' have smaller, upright and single, violet-blue colored flowers than plants of the wild type seedlings.
2. Plant of 'PKML01' have shorter and sturdier flower peduncles than plants of the wild type seedlings.
3. Plant of 'PKML01' are more compact and have more ascending stems in the center than plants of the wild type seedlings.
4. Plant of 'PKML01' have smaller but more flowers per plant than plants of the wild type seedlings.

BRIEF DESCRIPTION OF THE DRAWINGS

The accompanying colored photographs illustrate the overall appearance of the new cultivar 'PKML01', showing the colors as true as it is reasonably possible to obtain in colored reproductions of this type. Colors in the photographs may differ slightly from the color values cited in the detailed botanical description, which more accurately describe the actual colors of 'PKML01'.

DETAILED BOTANICAL DESCRIPTION

Figure 1:
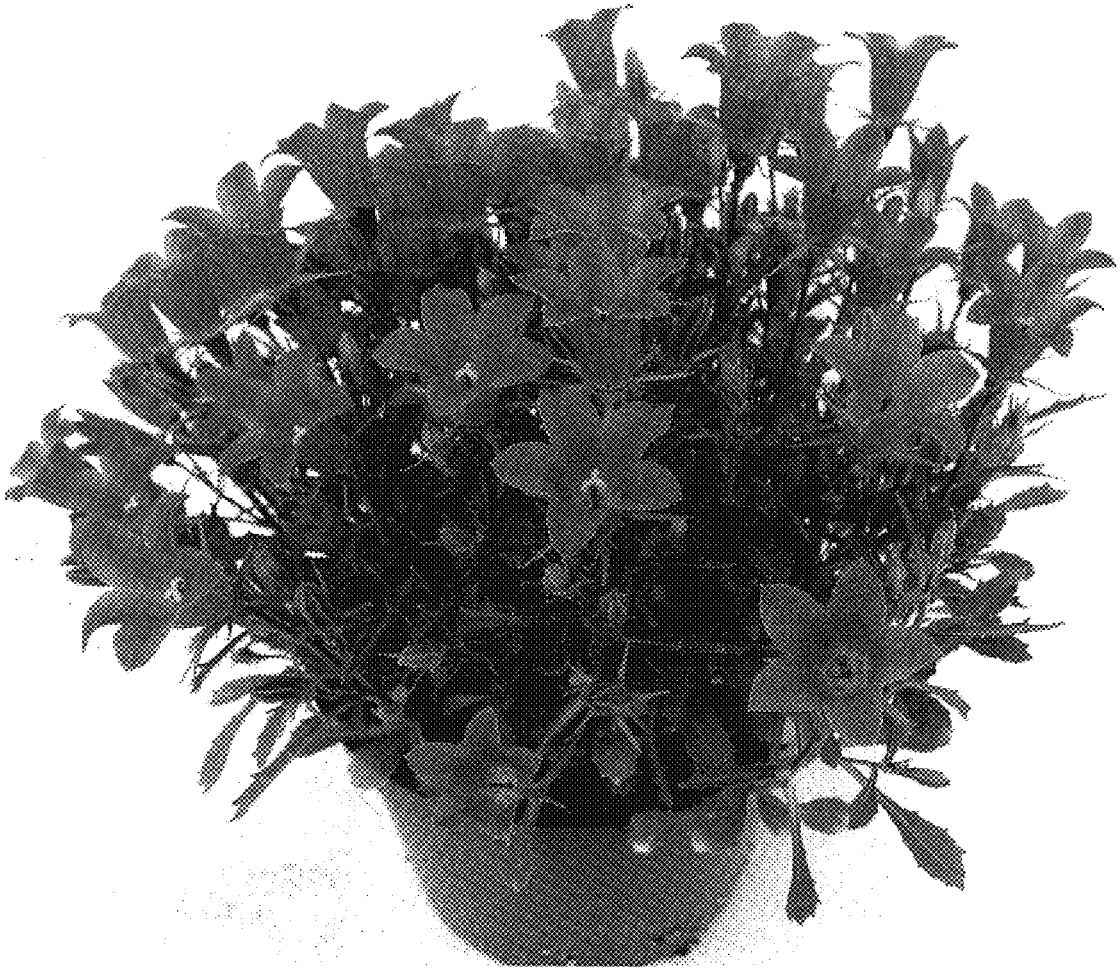
FIG. 1 shows a side perspective view of a typical flowering plant of 'PKML01' as grown in a 10.5 cm pot.
Figure 2:
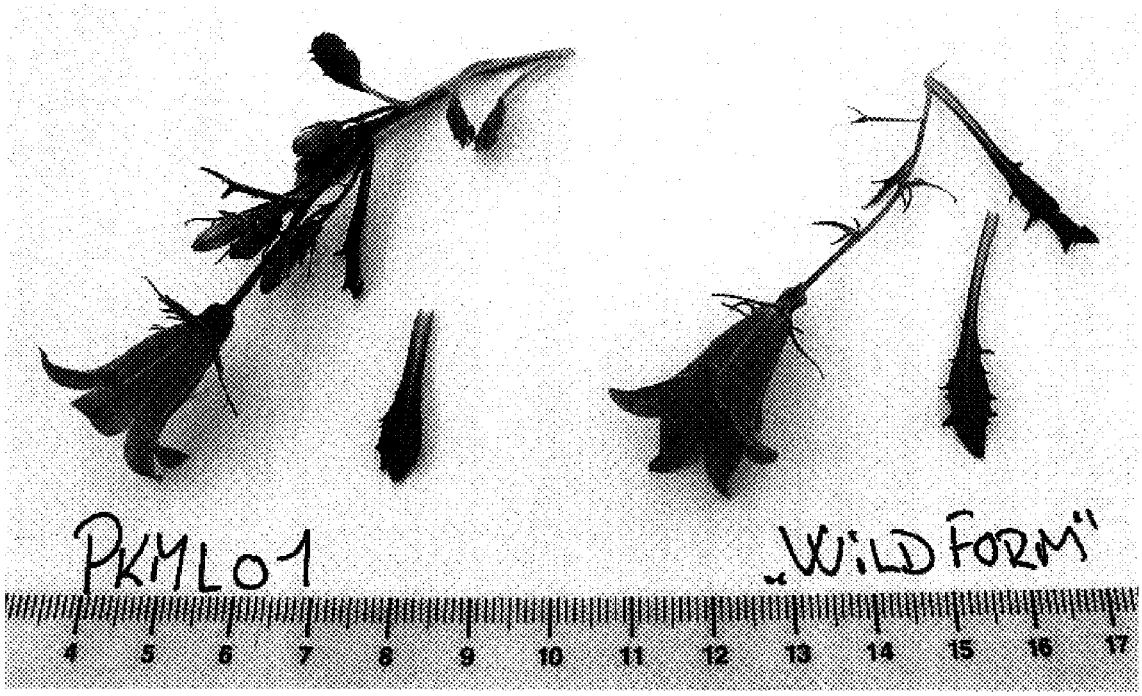
FIG. 2 shows a close-up view of a typical flowering raceme and leaf of 'PKML01' compared to a close-up view of a typical flowering raceme and leaf of the *Campanula lasiocarpa* wild type.

The new *Campanula* cultivar, 'PKML01' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* cultivar 'PKML01' as grown in a heated and lighted, glass-covered greenhouse in Søhus, Denmark, under conditions which closely approximate those generally used in commercial practice. Plants of 'PKML01' are grown in a glass-covered greenhouse where day temperatures in the greenhouse range from 18–20° C. and night temperatures in the greenhouse range from 16–18° C. Light levels used while growing 'PKML01' are 45 $Wm^2$, and plants of 'PKML01' are grown in long day conditions of 16–18 hours from the $10^{th}$ week after planting. The growth retardant used is 1 Bonzi.

The age of the 'PKML01' plants described is 16 weeks old (after cutting, being pinched twice, but not retarded) and grown in 10.5 cm pots. The photographs and descriptions were taken during the winter season when day temperatures in the glass-covered greenhouse range from 18–20° C. and when night temperatures in the glass-covered greenhouse range from 16–18° C.

Color references are made to The Royal Horticultural Society Colour Chart (R.H.S.), $4^{th}$ ed., except where general colors of ordinary significance are used.

Classification:

*Botanical.*—*Campanula lasiocarpa.*

Parentage:

Female parent.—*Campanula lasiocarpa* Cham. plant designated '2229' (unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright plant habit. Campanulate flowers in racemes. Freely branching with lateral branches forming at every node.

*Crop time.*—After rooting, about 16 weeks are required to produce finished flowering plants in 10.5 cm pots.

*Plant height* (*soil level to top of plant plane*).—About 14 cm.

*Plant spread* (*width*).—About 20 cm.

*Lateral branches.*—Quantity: About 40 per plant. Length (basal branches): 1–2 cm. Branch diameter: 1 mm. About 7–9 leaves per lateral branch.

*Internode length.*—About 25 mm at base and 10–22 mm higher up.

*Stem.*—Shape: Round. Strength: Moderately strong. Aspect: Upright. Color: RHS 144A, yellow-green.

*Vigor.*—Vigorous growth rate.

*Foliage description.*—Alternate, single pinnate venation. Basal leaves: Length: 45 mm. Width: 12 mm. Shape: Spatulate. Apex: Acute. Base: Attenuate to decussate. Margin: Slightly dentate. Texture: Glabrous, rugulose. Upper (Bracts) leaves: Length: 15–30 mm. Width: 4 mm. Shape: Gladiate. Apex: Aristulate. Base: Attenuate to decussate. Margin: Slightly dentate. Texture: Glabrous, rugulose. Color: Upper surfaces (young and mature foliage) RHS 137B, green; Under surfaces (young foliage) RHS 138C, green and (mature foilage) RHS 138B, green.

*Venation.*—Color: (upper surfaces) RHS 145B, yellow-green; (under surfaces) RHS 138B, green. Pattern: pinnate.

*Petiole.*—Basal Length: 15 mm. Upper (Bracts) Length: sessile. Diameter: 0.5 mm, flat, winged. Texture: pubescent. Color: RHS 145B, yellow-green.

Flower description:

*Flower number per plant.*—About 130.

*Flower arrangement and shape.*—Single, upright, acropetal flowers in racemes; campanulate single flowers with small star shaped calyx.

*Natural flowering season.*—Continuous throughout the spring and summer. Season can be extended year round by long day treatments.

*Time to flower.*—40 long days.

*Flower longevity on the plant.*—22 days; however, longevity of individual flowers is highly dependent on temperature and light conditions. Flowers persistent.

*Fragrance.*—None.

*Number of flowers per inflorescence.*—6.

*Number of flowers per lateral stem.*—6.

*Inflorescence size.*—Length: About 12 cm. Diameter: About 20 cm.

*Flowers.*—Aspect: Upright. Depth: 25 mm, including ovary. Diameter: 22–28 mm. Lanceolate to triangular, acute petal lobes: about 8 mm long and 7 mm wide.

*Corolla color.*—Uniform, RHS 94A to 94C, violet-blue.

*Buds.*—Length: up to 15 mm. Diameter: up to 5 mm. Shape: oblong, ridges.. Color: RHS 90B, violet-blue with ridges, RHS 91C, violet-blue.

*Petals.*—Arrangement: Single, sympetalous, campanulate. Appearance: Slightly rugulose. Quantity per flower: 5. Length: 7–9 mm. Width: 6–8 mm. Overall shape: Acute. Apex: Acute. Base: Fused. Margin: Entire. Texture: Velvety. Color (when opening): upper surface RHS 94A, violet-blue, and under surface RHS 94C, purple-violet. Color (when opened): upperside RHS 94C, violet-blue with central part of lobes RHS 94A, violet-blue, and underside RHS 94C, violet-blue. Fading to RHS 196D, gray-green.

*Sepals.*—Arrangement: Free. Appearance: Shiny, glabrous. Quantity per flower: 5. Length: 6–10 mm. Width: 1 mm. Overall shape: Gladiate with stipuleate bases. Apex: Acuminate. Base: Fused. Margin:

Whole. Color: (immature) upperside RHS 144B, yellow-green and underside RHS 139C, green. Color: (mature) upperside RHS 144A, yellow-green and underside RHS 139B, green.

*Peduncles.*—Length: About 45 mm. Diameter: 1 mm. Strength: Strong. Angle: 0 to 130 degrees from vertical. Color: 138A, green.

Reproductive organs:

*Androecium.*—Stamen: Quantity: 5, fused until pollen has been shed. Anther: Shape: Linear, with a groove. Length: About 5 mm. Color: RHS 11D, yellow. Pollen: Amount: Good production, plenty. Color: RHS 11B, yellow.

*Gynoecium.*—Pistil: Quantity: 1. Length: About 9 mm. Stigma: Shape: Tripartite. Color: RHS 158C, yellow-white. Style: Length: About 9 mm. Color: RHS 105A, blue. Ovary: Color: RHS 144D, yellow-green.

*Seeds.*—Quantity: 30 per flower. Length: About 1 mm. Diameter: About 0.1 mm. Texture: smooth and glabrous. Color: Immature, translucent RHS 155D, white. Color: Mature, RHS 175D, greyed-orange.

*Fruit.*—Type: Capsule. Length: About 6 to 8 mm. Diameter: About 2–3 mm. Color: RHS 164C, greyed-orange.

*Growth retardant.*—1 Bonzi (Paclobutrazol).

*Weather tolerance.*—Plants of the new *Campanula* have exhibited good tolerance to drought, rain and wind, with low temperature resistance to −15° C. and high temperature tolerance to 40° C.

Disease/pest resistance: 'PKML01' is not resistant to any diseases or pests typical to *Campanula* cultivars.

Disease/pest susceptibility: 'PKML01' is susceptible to *Botrytis.*

I claim:

1. A new and distinct cultivar of *Campanula* plant named 'PKML01', as illustrated and described herein.

* * * * *

UNITED STATES PATENT AND TRADEMARK OFFICE

CERTIFICATE OF CORRECTION

PATENT NO. : PP 17,225 P3
APPLICATION NO. : 11/059412
DATED : November 21, 2006
INVENTOR(S) : Gert Kim Jensen It is certified that error appears in the above-identified patent and that said Letters Patent is hereby corrected as shown below:

Title page
Correct the Title (54): delete '~~PKMIOL~~' and insert 'PKML01'

The Corrected Title should read:

CAMPANULA PLANT NAMED 'PKML01'

Signed and Sealed this

Twenty-seventh Day of February, 2007

JON W. DUDAS
*Director of the United States Patent and Trademark Office*